United States Patent
Williams, II.

(10) Patent No.: US 9,161,546 B2
(45) Date of Patent: Oct. 20, 2015

(54) INSECT REPELLING METHODS AND COMPOSITIONS

(76) Inventor: William R. Williams, II., Chapel Hill, NC (US)

(*) Notice: Subject to any disclaimer, the term of this patent is extended or adjusted under 35 U.S.C. 154(b) by 0 days.

(21) Appl. No.: 13/877,481

(22) PCT Filed: Oct. 3, 2011

(86) PCT No.: PCT/US2011/054586

§ 371 (c)(1),
(2), (4) Date: Apr. 3, 2013

(87) PCT Pub. No.: WO2012/047797

PCT Pub. Date: Apr. 12, 2012

(65) Prior Publication Data

US 2013/0209589 A1    Aug. 15, 2013

Related U.S. Application Data

(60) Provisional application No. 61/389,518, filed on Oct. 4, 2010.

(51) Int. Cl.
| | | |
|---|---|---|
| *A61K 36/889* | (2006.01) | |
| *A61K 36/58* | (2006.01) | |
| *A01N 65/40* | (2009.01) | |
| *A01N 65/00* | (2009.01) | |
| *A01N 65/08* | (2009.01) | |
| *A01N 65/26* | (2009.01) | |

(52) U.S. Cl.
CPC ............... *A01N 65/40* (2013.01); *A01N 65/00* (2013.01); *A01N 65/08* (2013.01); *A01N 65/26* (2013.01)

(58) Field of Classification Search
CPC ............................. A61K 36/18; A61K 36/58
See application file for complete search history.

(56) References Cited

U.S. PATENT DOCUMENTS

| | | | |
|---|---|---|---|
| 5,885,600 A * | 3/1999 | Blum et al. ............... | 424/405 |
| 2004/0018244 A1 * | 1/2004 | Piterski .................... | 424/535 |
| 2006/0188533 A1 * | 8/2006 | Brown et al. ............. | 424/401 |
| 2008/0305193 A1 | 12/2008 | Duprey, Jr. | |
| 2008/0317804 A1 * | 12/2008 | O'Brien ................... | 424/411 |
| 2009/0068128 A1 | 3/2009 | Waddington | |
| 2009/0214607 A1 | 8/2009 | Lintner et al. | |
| 2010/0197544 A1 | 8/2010 | De La Cruz | |

FOREIGN PATENT DOCUMENTS

| | | |
|---|---|---|
| DE | 10021560 A1 | 11/2001 |
| WO | WO 0185103 A1 * | 11/2001 |

OTHER PUBLICATIONS

Sharma et al. (1995) SE Asian Journal of Tropical Med. and Pub. Health vol. 26, No. 1 pp. 180-182.*
Website document entitled "Monoi Oil" (available at http://en.wikipedia.org/wiki/monoi_oil). Archived to Mar. 20, 2011 at http://web.archive.org. Downloaded from website Jun. 11, 2014.*
Sharma et al., "Field Studies on the Mosquito Repellent Action of Neem Oil", Southeast Asian Journal of Tropical Medicine and Public Health, Mar. 1995, pp. 180-182, vol. 26 No. 1 (abstract).
New Zealand Office Action dated Jan. 23, 2014 for Application No. 610195.

* cited by examiner

*Primary Examiner* — Chris R Tate
*Assistant Examiner* — Russell Fiebig
(74) *Attorney, Agent, or Firm* — Adam Wolek; Wolek & Noack

(57) ABSTRACT

Compositions and methods for repelling biting midges, sand flies, and mosquitoes comprising applying to human skin compositions comprising neem oil, coconut oil, jojoba oil, and monoi oil. This composition is non toxic to mammals, marine vertebrates or invertebrates and other forms of aquatic life.

5 Claims, No Drawings

INSECT REPELLING METHODS AND COMPOSITIONS

CROSS-REFERENCE TO RELATED APPLICATION

This application is a 35 U.S.C. §371 application of PCT/US2011/054586 filed Oct. 3, 2011, which claims the benefit of priority to U.S. provisional patent application Ser. No. 61/389,518 filed Oct. 4, 2010, each of which is incorporated herein by reference in its entirety.

FIELD OF INVENTION

Composition and methods for repelling biting midges, sand flies, and mosquitoes comprising applying to human skin compositions comprising neem oil, coconut oil, jojoba oil, and optionally monoi oil.

BACKGROUND OF THE INVENTION

Biting Midges, Sand Flies and disease vector mosquitoes are blood sucking insect pests that feed on humans and animals alike. Their bites can inflict minor irritation or itching welts lasting for several days. In worse case scenarios, infections or diseases such as Leishmaniasis, Malaria, Dengue Fever or Yellow Fever can result.

The biting midge is known as the primary pest in the Caribbean and is a deterrent for tourism due to the lack of effective solutions to repel the pests and their bothersome bites. The sand fly is another pest prevalent in almost every Caribbean area. Bites from either the biting midge or sand fly can also cause irritation, discomfort and annoyance, and also deter tourism. There are also several forms of mosquito's present in the Caribbean. The largest threats to humans are the mosquitoes of the genera *Anopheles, Aedes* and *Culex*, which can carry Malaria, Dengue and Yellow Fever. In recent years, instances of Dengue fever have risen dramatically. Many insecticides utilized to combat biting midges and sand flies are ineffective or insufficiently effective as repellents.

Furthermore, many of the pesticides utilized to repel insects contaminate water sources and are toxic to various forms of marine life in aquatic or ocean environments. Toxicity concerns are particularly important in the Caribbean since many insecticides and pesticides flow into water sources that lead to the ocean. Moreover, marine life such as coral, vertebrates and invertebrates are very sensitive to toxic pesticides. Exacerbating this problem is that many sun bathers, swimmers, divers and snorkelers often do not wash off toxic pesticides prior to nearing aquatic or ocean environments. Additionally, the water used to wash off the toxic pesticides often contains the residues of the pesticides, which may run off or drain into the aquatic environments.

For these and other reasons, there is a long felt need for pesticides that are non-toxic to marine life, are biodegradable, and that have no known negative environmental impacts. Compositions that are non-toxic to mammals, aquatic or marine life are especially important environmentally due to sensitivity of water sources

SUMMARY OF THE INVENTION

Compositions comprising neem oil, coconut oil, jojoba oil, and optionally monoi oil are effective for repelling biting midges, sand flies, and mosquitoes when applied to human skin, are non-toxic to marine life, are biodegradable, and have no known negative environmental impacts.

A method for repelling biting midges, sand flies and mosquitoes comprises applying to human skin compositions comprising neem oil and coconut oil.

Another method for repelling biting midges, sand flies and mosquitoes comprises applying to human skin compositions comprising neem oil, coconut oil, and jojoba oil.

Yet another method for repelling biting midges, sand flies and mosquitoes comprises applying to human skin compositions comprising neem oil, coconut oil, jojoba oil, and monoi oil.

DETAILED DESCRIPTION

The present invention relates to stable and biodegradable compositions comprising oils blended in a manner providing insect repelling properties that are non-toxic to mammals, marine vertebrates or invertebrates and other forms of aquatic life. The invention provides a synergistic mixture of neem oil and other oils that repels insects. This composition can be used for dermal application to humans as an insect repellent.

The invention further relates to methods of repelling insects from humans by applying to human skin compositions comprising neem oil and coconut oil.

The composition can further comprise at least one of jojoba oil, monoi oil, almond oil, tea tree oil, castor oil, cedar oil, cinnamon oil, citric acid, citronella oil, clove oil, corn oil, cottonseed oil, garlic oil, geranol, geranium oil, lauryl sulfate, lemongrass oil, linseed oil, malic acid, mint oil, peppermint oil, 2-phenethyl propionate, potassium sorbate, rosemary oil, sesame oil, soybean oil, thyme oil, palm oil, wheat oil, wheat germ oil, white mineral oil, argon nut oil, avocado oil, babassu oil, borage oil, canola oil, evening primrose oil, flax seed oil, grape seed oil, hemp seed oil, macadamia nut oil, olive oil, pomegranate oil, pumpkin seed oil, safflower oil, soy bean oil and sunflower oil, apricot oil, black cumin oil, black currant oil, rapeseed oil, cherry kernel oil, hazelnut oil, kukui nut oil, peach kernel oil, pecan oil, perilla seed oil, pistachio oil, pomegranate oil, rice bran oil, rosehip oilsea buckthorn oil, squalane oil, and walnut oil.

The invention further relates to methods of repelling insects from humans by applying to human skin compositions comprising neem oil, coconut oil, jojoba oil and monoi oil.

Neem oil is cold pressed directly from seeds of the Neem tree (*Azadirachta indica*), which is a tropical evergreen tree native to India and also found in other Southeast Asian and African countries. Cold Pressed Neem Oil has a brown color, a bitter taste and a garlic/sulfur smell.

Coconut oil is extracted via a cold pressed method from the kernel or meat of matured coconuts harvested from the coconut palm. The coconut (*Cocos nucifera*) is a member of the family Arecaceae (palm family) and is indigenous to tropical climates worldwide.

Jojoba oil is a cold pressed extract from the Jojoba tree (*Simmondsia chinensis*) and comprises long chain monosaturated wax esters. It is extensively used in specialty cosmetics The addition of Jojoba oil adds moisturizing properties, aids in the absorption process and surprisingly reduced the solidification temperature of the mixture.

Monoi oil is a combination of pure cold pressed coconut oil and the infused fragrance of the Tiare flower, which is extracted from crushed leaves of the Tahitian Tiare flower (*Gardenia Taitensis*).

The composition of neem oil, coconut oil, jojoba oil and monoi oil provides for a synergistic combination exhibiting surprising properties. For instance, the synergistic composition creates a repellent effectiveness greater than their individual parts and that is not apparent in other formulations. The composition also creates an appealing texture for application. The composition provides for smooth and even distribution over human skin. Other compositions can produce greasy or sticky textures, and can also produce uneven coverage.

Neem oil has a very pungent garlic aroma that is unappealing for use on human skin. However, the composition of the present invention surprisingly provides an appealing aroma by mitigating and/or masking the neem oil scent.

Neem oil and coconut oil compositions have solubility and hardening issues on storage in temperatures below 76 degrees. This can create undesirable side effects that limit the composition's uses. It can also create unsightly floating solids. The addition of jojoba and/or monoi oil creates a synergistic composition that decreases the solidification temperature of the mixture and also increases the liquefaction response to heat of the mixture once solidified, thereby increasing the composition's uses and marketability.

The synergistic composition offers skin protection and softening effectiveness not apparent in other formulations.

The above compositions are directed to repelling biting midges of the genra *Culicoides* and *Leptocanops* (Biting Midge or "no-see-urn") native to the Caribbean; the Leishmaniasis vector sand fly Genus *Lutzomyia* (Phlebotominae Sand Fly); the sand fly Genus *Lutzomyia* (Phlebotominae Sand Fly) with the following species *aclydifera, apicalis, arborealis, barrattoi, beltrani, bispinoa, carpenteri, cayennensis, chiapenensis, craftier, cruciata, cunhai, deleoni, durani, evansi, gomezi*, longipalpis*, olmeca*, ovallesi*, panamensis*, paraensis, sanguinaria, shannoni, texana, trapidoi*, trinidadensis, undulata, ylephiletor*;* the sand fly Genus *Brumptomyia* (Phlebotominae Sand Fly); the sand fly Genus *Brumptomyia galindoi* (Phlebotomine Sand Fly); the mosquitoes of the Genus *Anopheles*; the malaria vector mosquito of the Genus *Anopheles Nyssorhynchus Albimanus*; the malaria vector mosquito of the Genus *Anopheles Anopheles pseudopunctipennis*; the malaria vector mosquito of the Genus *Anopheles Nyssorhynchus darlingi*; the mosquitoes of the Genus *Aedes*; the Dengue and Yellow Fever arbovirus vector mosquito of the Genus *Aedes Stegomyia aegypti*; the mosquitoes of the Genus *Culex*; the Encephalitis arbovirus vector mosquito of the Genus *Culex Culex nigripalpus*; the Encephalitis arbovirus vector mosquito of the Genus *Culex Culex quiquefasciatus*; the Encephalitis arbovirus vector mosquito of the Genus *Culex Culex restuans*; and mosquitoes of the Genera *Aedomyia, Coquilletidia, Culicinae, Deinocerites, Haemagogus, Limatus, Mansonia, Psorophora, Sabethes, Toxorhynbhites, Trichoprosopon, Johnbelkinia, Uranotaenia,* and *Wyeomyia*.

A preferred embodiment of the present invention comprises 0.2% to 30% neem oil by volume and a single one or combination of more inert oils comprising 70% to 99.8% by volume. Another preferred composition of the present invention comprises 0.2% to 30% neem oil and 70% to 99.8% coconut oil. A more preferred embodiment comprises 0.2% to 10% neem oil by volume and 90% to 99.8% coconut oil by volume. Yet another preferred embodiment comprises 2% to 6% neem oil by volume and 94% to 98% coconut oil by volume.

Another preferred embodiment of the present invention comprises 0.2% to 30% neem oil, 50% to 94.8% coconut oil, and 5% to 49.8% jojoba oil. Yet another preferred embodiment of the present invention comprises 1% to 10% neem oil, 50% to 94% coconut oil, and 5% to 49% jojoba oil. A more preferred embodiment of the present invention comprises 2% to 6% neem oil, 50% to 93% coconut oil, and 5% to 48% jojoba oil.

Another preferred embodiment of the present invention comprises 0.2% to 30% neem oil, 50% to 94.8% coconut oil, 5% to 49.6% jojoba oil, and 0.2% to 30% monoi oil. Yet another preferred embodiment of the present invention comprises 1% to 10% neem oil, 50% to 94% coconut oil, 5% to 48.8% jojoba oil, 0.2% to 30% monoi oil. A more preferred embodiment of the present invention comprises 2% to 6% neem oil, 50% to 92.8% coconut oil, 5% to 47.8% jojoba oil, 2% to 30% monoi oil.

Another preferred embodiment of the present invention comprises 0.2% to 30% neem oil, 50% to 98.6% jojoba oil and 0.2% to 30% monoi oil. Yet another preferred embodiment of the present invention comprises 1% to 10% neem oil, 50% to 98.8% jojoba oil and 0.2% to 30% monoi oil. A more preferred embodiment of the present invention comprises 2% to 6% neem oil, 50% to 97.8% jojoba oil and 0.2% to 30% monoi oil.

Another embodiment of the present invention comprises 0.2% to 30% neem oil, 50% to 94.6% coconut oil, 5% to 49.6% jojoba oil, and 0.2% to 30% kukui oil. Yet another preferred embodiment of the present invention comprises 1% to 10% neem oil, 50% to 94% coconut oil, 5% to 48.8% jojoba oil, and 0.2% to 30% kukui oil. A more preferred embodiment of the present invention comprises 2% to 6% neem oil, 50% to 92.8% coconut oil, 5% to 47.8% jojoba oil, and 0.2% to 30% kukui oil.

Another preferred composition comprises 0.2% to 30% neem oil and 70% to 99.8% by volume of one or more of the following oils: jojoba oil, monoi oil, almond oil, castor oil, cedar oil, cinnamon oil, citric acid, citronella oil, clove oil, coconut oil, corn oil, cottonseed oil, garlic oil, geranol, geranium oil, lauryl sulfate, lemongrass oil, linseed oil, malic acid, mint oil, peppermint oil, 2-phenethyl propionate, potassium sorbate, rosemary oil, sesame oil, soybean oil, thyme oil, palm oil, wheat oil, wheat germ oil, white mineral oil, argon nut oil, avocado oil, babassu oil, borage oil, canola oil, evening primrose oil, flax seed oil, grape seed oil, hemp seed oil, macadamia nut oil, olive oil, pomegranate oil, pumpkin seed oil, safflower oil, soy bean oil, sunflower oil, apricot oil, black cumin oil, black currant oil, rapeseed oil, cherry kernel oil, hazelnut oil, kukui nut oil, peach kernel oil, pecan oil, perilla seed oil, pistachio oil, pomegranate oil, rice bran oil, rosehip oil, sea buckthorn oil, squalane oil, walnut oil, and tee tree oil.

And yet another preferred composition of the oils comprises 0.2% to 15% Neem oil, 0.2% to 15% Monoi oil, 0.05% to 60% Jojoba oil and 10% to 99.55% Coconut oil.

A different preferred composition of the present invention comprises 0.2% to 30% neem oil and 70% to 99.8% jojoba oil.

Another different preferred composition of the present invention comprises 0.2% to 30% neem oil and 70% to 99.8% monoi oil.

Yet another preferred embodiment of the present invention comprises 0.2% to 30% neem oil, 35% to 94.6% coconut oil, 5% to 49.6% jojoba oil, and 0.2% to 30% kukui oil.

And yet another preferred embodiment of the present invention comprises 0.2% to 30% neem oil, 40% to 99.6% jojoba oil and 0.2% to 30% monoi oil.

A preferred method of repelling biting midges genus (*Culicoides*) or "no-see-um" comprises applying compositions comprising neem oil and coconut oil to human skin.

A preferred method of repelling biting midges genera *Culicoides*, and *Leptocanops* comprises applying to human skin compositions comprising 2% to 10% neem oil and 90% to 98% coconut oil.

A preferred method of repelling biting midges genera *Culicoides*, and *Leptocanops* comprises applying to human skin compositions comprising 2% to 10% neem oil, 50% to 93% coconut oil, and 5% to 48% jojoba oil.

A preferred method of repelling biting midges genera *Culicoides*, and *Leptocanops* comprises applying to human skin compositions comprising 2% to 10% neem oil, 50% to 91% coconut oil, 5% to 48% jojoba oil, and 2% to 30% monoi oil.

A preferred method of repelling biting midges genera *Culicoides* and *Leptocanops* comprises applying to human skin compositions comprising 2% to 10% neem oil and 90% to 98% jojoba oil.

A preferred method of repelling biting midges of the genera *Culicoides*, and *Leptocanops* comprises applying to human skin compositions comprising 2% to 10% neem oil and 90% to 98% monoi oil.

A preferred method of repelling biting midges of the genera *Culicoides*, and *Leptocanops* comprises applying to human skin compositions comprising 2% to 10% neem oil, 60% to 96% jojoba oil and 2% to 30% monoi oil.

A preferred method of repelling biting midges of the genera *Culicoides*, and *Leptocanops* comprises applying to human skin compositions comprising 2% to 10% neem oil, 55% to 91% coconut oil, 5% to 46% jojoba oil, and 2% to 30% kukui oil.

A preferred method of repelling biting midges of the genera *Culicoides*, and *Leptocanops* comprises applying to human skin compositions comprising 2% to 10% neem oil and 90% to 98% by volume of one or more of the following oils: jojoba oil, monoi oil, almond oil, castor oil, cedar oil, cinnamon oil, citric acid, citronella oil, clove oil, coconut oil, corn oil, cottonseed oil, garlic oil, geranol, geranium oil, lauryl sulfate, lemongrass oil, linseed oil, malic acid, mint oil, peppermint oil, 2-phenethyl propionate, potassium sorbate, rosemary oil, sesame oil, soybean oil, thyme oil, palm oil, wheat oil, wheat germ oil, white mineral oil, argon nut oil, avocado oil, babassu oil, borage oil, canola oil, evening primrose oil, flax seed oil, grape seed oil, hemp seed oil, macadamia nut oil, olive oil, pomegranate oil, pumpkin seed oil, safflower oil, soy bean oil and sunflower oil, apricot oil, black cumin oil, black currant oil, rapeseed oil, cherry kernel oil, hazelnut oil, kukui nut oil, peach kernel oil, pecan oil, perilla seed oil, pistachio oil, pomegranate oil, rice bran oil, rosehip oilsea buckthorn oil, squalane oil, walnut oil, and tee tree oil.

A preferred method of repelling Genus *Lutzomyia* (Phlebotominae Sand Fly) and the sand fly Genus *Lutzomyia* with the following species *aclydifera, apicalis, arborealis, barrattoi, beltrani, bispinoa, carpenteri, cayennensis, chiapenensis, craftier, cruciata, cunhai, deleoni, durani, evansi, gomezi\*, longipalpis\*, olmeca\*, ovallesi\*, panamensis\*, paraensis, sanguinaria, shannoni, texana, trapidoi\*, trinidadensis, undulata, ylephiletor\**; and the sand fly Genus *Brumptomyia* (Phlebotomine Sand Fly) including species *Brumptomyia galindoi* (Phlebotominae Sand Fly); the sand fly Genus *Phlebotomus* (Phlebotominae Sand Fly); comprises applying to human skin compositions comprising 2% to 10% neem oil and 90% to 98% coconut oil. Another preferred method of repelling members of the Genus *Lutzomyia* and *Brumptomyia* comprises applying to human skin compositions comprising 2% to 10% neem oil, 50% to 93% coconut oil, and 5% to 48% jojoba oil.

A preferred method of repelling members of the genera *Lutzomyia*, *Brumptomyia* and *Phlebotomus* comprises applying to human skin compositions comprising 2% to 10% neem oil, 50% to 91% coconut oil, 5% to 48% jojoba oil, and 2% to 30% monoi oil.

A preferred method of repelling Genus *Lutzomyia* comprises applying to human skin compositions comprising 2% to 10% neem oil and 90% to 98% jojoba oil.

A preferred method of repelling members of the genera *Lutzomyia* and *Brumptomyia* comprises applying to human skin compositions comprising 2% to 10% neem oil and 90 to 98% monoi oil.

A preferred method of repelling members of the genera *Lutzomyia*, *Phlebotomus* and *Brumptomyia* comprises applying to human skin compositions comprising 2% to 10% neem oil, 60% to 96% jojoba oil and 2% to 30% monoi oil.

A preferred method of repelling members of the genera *Lutzomyia*, *Phlebotomus* and *Brumptomyia* comprises applying to human skin compositions comprising 2% to 10% neem oil, 50% to 91% coconut oil, 5% to 48% jojoba oil, and 2% to 30% kukui oil.

A preferred method of repelling members of the genera *Lutzomyia*, *Phlebotomus*, and *Brumptomyia* comprises applying to human skin compositions comprising 2% to 10% neem oil and 90% to 98% by volume of one or more of the following oils: jojoba oil, monoi oil, almond oil, castor oil, cedar oil, cinnamon oil, citric acid, citronella oil, clove oil, coconut oil, oil, cottonseed oil, garlic oil, geranol, geranium oil, lauryl sulfate, lemongrass oil, linseed oil, malic acid, mint oil, peppermint oil, 2-phenethyl propionate, potassium sorbate, rosemary oil, sesame oil, soybean oil, thyme oil, palm oil, wheat oil, wheat germ oil, white mineral oil, argon nut oil, avocado oil, babassu oil, borage oil, canola oil, evening primrose oil, flax seed oil, grape seed oil, hemp seed oil, macadamia nut oil, olive oil, pomegranate oil, pumpkin seed oil, safflower oil, soy bean oil, sunflower oil, apricot oil, black cumin oil, black currant oil, rapeseed oil, cherry kernel oil, hazelnut oil, kukui nut oil, peach kernel oil, pecan oil, perilla seed oil, pistachio oil, pomegranate oil, rice bran oil, rosehip oil, sea buckthorn oil, squalane oil, walnut oil, and tee tree oil.

A preferred method of repelling mosquitoes of the Genus *Anopheles* and species *Anopheles Nyssorhynchus Albimanus*; species *Anopheles Anopheles pseudopunctipennis*; species *Anopheles Nyssorhynchus darlingi*; the mosquitoes of the Genus *Aedes*; species *Aedes Stegomyia aegypti*; the mosquitoes of the Genus *Culex*; species *Culex Culex nigripalpus*; species *Culex Culex quiquefasciatus*; species *Culex Culex restuans*; mosquitoes of the Genus *Aedomyia*; mosquitoes of the Genus *Coquilletidia*; mosquitoes of the Genus *Culicinae*; mosquitoes of the Genus *Deinocerites*; mosquitoes of the Genus *Haemagogus*; mosquitoes of the Genus *Limatus*; mosquitoes of the Genus *Mansonia*; mosquitoes of the Genus *Psorophora*; mosquitoes of the Genus *Sabethes*; mosquitoes of the Genus *Toxorhynbhites*; mosquitoes of the Genus *Trichoprosopon*; mosquitoes of the Genus *Johnbelkinia*; mosquitoes of the Genus *Uranotaenia*; mosquitoes of the Genus *Wyeomyia* comprises applying to human skin compositions comprising 2% to 10% neem oil and 90% to 98% coconut oil.

A preferred method of repelling mosquitoes of the genera *Anopheles, Aedes, Culex, Aedomyia, Coquilletidia, Culicinae, Deinocerite, Haemagogus, Limatus, Mansonia, Psorophora, Sabethes, Toxorhynbhites, Trichoprosopon, Johnbelkinia, Uranotaenia*, and/or *Wyeomyia* comprises applying to human skin compositions comprising 2% to 10% neem oil, 50% to 93% coconut oil, and 5% to 48% jojoba oil.

A preferred method of repelling mosquitoes of the genera *Anopheles, Aedes, Culex, Aedomyia, Coquilletidia, Culicinae, Deinocerite, Haemagogus, Limatus, Mansonia, Psorophora, Sabethes, Toxorhynbhites, Trichoprosopon, Johnbelkinia, Uranotaenia*, and/or *Wyeomyia* comprises applying to human skin compositions comprising 2% to 10% neem oil, 55% to 91% coconut oil, 5% to 48% jojoba oil, and 2% to 30% monoi oil.

A preferred method of repelling mosquitoes of the genera *Anopheles, Aedes, Culex, Aedomyia, Coquilletidia, Culicinae, Deinocerite, Haemagogus, Limatus, Mansonia, Psorophora, Sabethes, Toxorhynbhites, Trichoprosopon, Johnbelkinia, Uranotaenia*, and/or *Wyeomyia* comprises applying to human skin compositions comprising 2% to 10% neem oil and 90 to 98% jojoba oil.

A preferred method of repelling mosquitoes of the genera *Anopheles, Aedes, Culex, Aedomyia, Coquilletidia, Culicinae, Deinocerite, Haemagogus, Limatus, Mansonia, Psorophora, Sabethes, Toxorhynbhites, Trichoprosopon, Johnbelkinia, Uranotaenia*, and/or *Wyeomyia* comprises applying to human skin compositions comprising 2% to 10% neem oil and 90% to 98% monoi oil.

A preferred method of repelling mosquitoes of the genera *Anopheles, Aedes, Culex, Aedomyia, Coquilletidia, Culicinae, Deinocerite, Haemagogus, Limatus, Mansonia, Psorophora, Sabethes, Toxorhynbhites, Trichoprosopon, Johnbelkinia, Uranotaenia*, and/or *Wyeomyia* comprises applying to human skin compositions comprising 2% to 10% neem oil, 60% to 96% jojoba oil and 2% to 30% monoi oil.

A preferred method of repelling mosquitoes of genera *Anopheles, Aedes, Culex, Aedomyia, Coquilletidia, Culicinae, Deinocerite, Haemagogus, Limatus, Mansonia, Psorophora, Sabethes, Toxorhynbhites, Trichoprosopon, Johnbelkinia, Uranotaenia*, and/or *Wyeomyia* comprises applying to human skin compositions comprising 2% to 10% neem oil, 50 to 91% coconut oil, 5% to 46% jojoba oil, and 2% to 30% kukui oil.

A preferred method of repelling mosquitoes of the genera *Anopheles, Aedes, Culex, Aedomyia, Coquilletidia, Culicinae, Deinocerite, Haemagogus, Limatus, Mansonia, Psorophora, Sabethes, Toxorhynbhites, Trichoprosopon, Johnbelkinia, Uranotaenia*, and/or *Wyeomyia* comprises applying to human skin compositions comprising 2% to 10% neem oil and 90% to 98% by volume of one or more of the following oils: jojoba oil, monoi oil, almond oil, castor oil, cedar oil, cinnamon oil, citric acid, citronella oil, clove oil, coconut oil, corn oil, cottonseed oil, garlic oil, geranol, geranium oil, lauryl sulfate, lemongrass oil, linseed oil, malic acid, mint oil, peppermint oil, 2-phenethyl propionate, potassium sorbate, rosemary oil, sesame oil, soybean oil, thyme oil, palm oil, wheat oil, wheat germ oil, white mineral oil, argon nut oil, avocado oil, babassu oil, borage oil, canola oil, evening primrose oil, flax seed oil, grape seed oil, hemp seed oil, macadamia nut oil, olive oil, pomegranate oil, pumpkin seed oil, safflower oil, sunflower oil, apricot oil, black cumin oil, black currant oil, rapeseed oil, cherry kernel oil, hazelnut oil, kukui nut oil, peach kernel oil, pecan oil, perilla seed oil, pistachio oil, pomegranate oil, rice bran oil, rosehip oil, sea buckthorn oil, squalane oil, walnut oil, and tee tree oil.

The formulations may be applied by spreading, spraying, pouring, dipping, direct application, and the like. They may be applied, for example, as specified above, in the form of dilute solution, in a suitable natural solvent, and directly on human skin, clothing, blankets, mosquito nets, hammocks, beds, and on tents.

Unless otherwise specified, all percentages refer to volume by volume measurements, and all temperature refers to Fahrenheit.

Unless otherwise specified, the use of "*" indicates a vector carrying species.

As used herein, all numerical values relating to amounts, weight percentages, and the like are defined as "about" or "approximately" each particular value, plus or minus 10%. Therefore, amounts within 10% of the claimed values are encompassed by the scope of the claims.

The following examples are offered by way of illustration only and not by way of limitation.

EXAMPLES

Testing on two occasions on the island of Roatan, Honduras was performed using a 2% neem oil and 98% coconut oil composition in June 2010. A second test on Roatan occurred in September 2010 utilizing two different compositions. The first was a 3.4% neem oil and 96.6% virgin organic coconut oil composition. The second was a 6% neem oil and 94% virgin organic coconut oil composition. The compositions were effective for up to 5 hours with about 100% effectiveness against biting midges, sand flies and mosquitoes. Reapplication after water exposure or heavy perspiration assured continued effectiveness of about 100% against biting midges, sand flies and mosquitoes. The mixture was greasy and sticky during and after application.

Mixtures of up to 10% neem oil and 90% coconut oil have been found effective in tests in Chapel Hill, N.C. against the local *Culex* mosquito. Several compositions have proven partially effective against the *Culex* mosquito in North Carolina for up to 2 hours in heavy exertion situations. A composition of 10% neem oil and 90% coconut oil was about 100% effective against bites for 4 hours. However, the composition emitted an unpleasant and undesirable aroma along with a greasy sensation once applied. In contrast, compositions comprising 3% to 6% neem oil, 94% to 97% coconut yielded similar repellent results under the same testing conditions but surprisingly maintained and exhibited a pleasant aroma.

Three further tests in Chapel Hill, N.C. yielded surprising results. The first occurred with about 95% bite protection and minimal lighting/landing with percentages of 3.3% of neem oil in combination with 16.6% jojoba oil, 80.1% coconut oil. The second test utilized a 3.4% neem oil, 3.4% tea tree oils, 30.6% Jojoba oil and 62.6% coconut oil composition. Bite protection percentages were about 95% with minimal lighting and landing characteristics of the mosquitoes. The aroma of the mixture was unpleasant and undesirable. The final test utilized a composition of 3.3% neem oil, 3.3% monoi oil, 16.6% Jojoba oil and 76.8% coconut oil. This mixture resulted in the best overall results with about 100% bite protection and minimal lighting or landing of the mosquitoes on the skin. The aroma is pleasant and desirable and application was smooth without the greasy feeling. It was also surprisingly noticed that the mixture solidified at temperatures that were several degrees lower. It was also easier to return the mixture to a liquid state after solidifcation. All compositions lasted from 1-3 hours, with variations attributed to temperature and level of exertion.

In further tests, the synergistic composition of about 3.3% neem oil, about 3.3% monoi oil, about 16.6% Jojoba oil and about 76.8% coconut oil surprisingly reduced the temperature of solidification of the mixture by up to 6 degrees when the jojoba and monoi oils were added. Liquefaction time from the solidified state at lower temperatures was also dramatically reduced, thus reducing the time it took the mixture to return to a usable liquid state. The mixture was placed in temperatures ranging from 58 to 74 degrees. Minimal solidification of about 1% to about 2% occurred until temperatures dropped below 68 degrees. In contrast, the neem oil and coconut oil alone solidify at approximately about 74 to about 76 degrees. An additional positive result from this synergistic mixture was the elimination of the unpleasant and undesirable aroma of the neem oil. Furthermore, the neem oil, monoi oil, jojoba oil and coconut oil provided a significantly greater ease of application and absorption than compositions comprising neem oil without monoi oil, jojoba oil and coconut oil added.

In another test, two different 8 fl.oz. compositions were taken from 70 degrees to 78 degrees comparing liquefaction times. This test was performed in triplicates. After 3 hours, about 1% of coconut oil was liquid, and about 100% of the neem oil, monoi oil, jojoba oil and coconut oil composition was liquid. In another test that was performed in triplicates, 8 fl.oz. samples of coconut oil when taken from 70 degrees to 78 degrees took 12 hours to be about 25% liquid, and 24 hours to be about 100% liquid. In contrast, neem oil, monoi oil, jojoba oil and coconut oil compositions took 1.25 hours to be about 25% liquid, and 2.75 hours to be about 100% liquid.

In a test comparing solidification times, two different 8 fl.oz. compositions were taken from 82 degrees to 72 degrees. This test was performed in triplicates. After 7 hours, about 100% of the coconut oil composition was solidified, and less than about 1% of the neem oil, monoi oil, jojoba oil and coconut oil composition was solid.

The invention claimed is:

1. A composition for repelling bloodsucking insects, said composition consisting essentially of about 2% to about 6% by volume of neem oil, from about 50% to about 92.8% by volume of coconut oil, from about 5% to about 47.8% by volume of jojoba oil, and from about 2% to about 30% by volume of monoi oil.

2. A composition for repelling bloodsucking insects, said composition comprising about 3.3% by volume of neem oil, about 76.8% by volume of coconut oil, about 16.6% by volume of jojoba oil, and about 3.3% by volume of monoi oil.

3. A method for repelling a bloodsucking insect from an individual exposed to said insect, comprising applying an effective amount of the composition of claim 1 to said individual or to said individual's clothing, blanket, mosquito net, hammock, bed, and/or tent.

4. The method of claim 3, wherein said bloodsucking insect is selected from the group consisting of biting midge, sand fly and mosquito.

5. The method of claim 3, wherein said composition is applied to the skin of said individual by spreading, spraying, or pouring the composition onto the individual's skin, or by dipping the individual's skin in the composition.

* * * * *